United States Patent [19]

Mallo et al.

[11] Patent Number: 5,360,881
[45] Date of Patent: Nov. 1, 1994

[54] METHOD OF CROSS-LINKING ETHYLENE MONOMERS USING DIALLYLOXYACETIC ACID AND ITS BASIC ADDITION SALTS AS CROSS-LINKING AGENTS

[75] Inventors: Paul Mallo, Rueil Malmaison; Christian Sidot, Ezanville; Alain Blanc, Saint Denis; Yani Christidis, Paris, all of France

[73] Assignee: Societe Francaise Hoechst, Puteaux, France

[21] Appl. No.: 65,446

[22] Filed: May 24, 1993

Related U.S. Application Data

[60] Division of Ser. No. 837,706, Feb. 20, 1992, abandoned, which is a continuation of Ser. No. 529,793, May 29, 1990, abandoned.

[30] Foreign Application Priority Data

Jun. 14, 1989 [FR] France ................... 89 07894

[51] Int. Cl.$^5$ .................. C08F 220/04; C08F 2/16
[52] U.S. Cl. .................. 526/240; 526/215; 526/229; 526/287; 526/318.1; 526/312; 562/579; 562/587
[58] Field of Search .............. 526/215, 229, 318.1, 526/240, 287, 295, 312

[56] References Cited

U.S. PATENT DOCUMENTS

| | | | |
|---|---|---|---|
| 2,340,111 | 1/1944 | D'Alelio | 526/318.1 |
| 3,582,512 | 6/1971 | Fantl | 526/318.1 |
| 4,027,082 | 5/1977 | Gavrilova | 526/318.1 |
| 4,070,368 | 1/1978 | Carson | 260/326.47 |
| 4,179,453 | 12/1979 | Johnston | 260/397.1 |
| 4,454,065 | 6/1984 | Gilvarg et al. | 562/556 |
| 4,845,122 | 7/1989 | Georgiev et al. | 514/472 |
| 4,871,842 | 10/1989 | Sugihara et al. | 540/523 |
| 4,962,099 | 10/1990 | Mosbach et al. | 514/177 |
| 4,962,099 | 10/1990 | Mosbach et al. | 514/177 |
| 4,985,514 | 1/1991 | Kimura | 526/88 |

OTHER PUBLICATIONS

Holmquist, L., Acta Chemica Scandinavica, 23 (1969), pp. 1045–1052 CA 81(11):46099h.

*Primary Examiner*—Christopher Henderson
*Attorney, Agent, or Firm*—Browdy and Neimark

[57] ABSTRACT

Diallyloxyacetic acid and its basic addition salts, their preparation process and their application as cross-linking agents.

Diallyloxyacetic acid and its basic addition salts, preparation process and application as cross-linking agents.

6 Claims, No Drawings

5,360,881

METHOD OF CROSS-LINKING ETHYLENE MONOMERS USING DIALLYLOXYACETIC ACID AND ITS BASIC ADDITION SALTS AS CROSS-LINKING AGENTS

This application is a division of co-pending application Ser. No. 07/837,706, filed Feb. 20, 1992, now abandoned without prejudice, itself a continuation of its co-pending parent application Ser. No. 07/529,793, filed May 29, 1990, now abandoned without prejudice.

BACKGROUND OF THE INVENTION

1. Field of the Invention

The present invention relates to diallyloxyacetic acid and its basic addition salts, their preparation process and their application as cross-linking agents.

Cross-linking agents are currently used to access polymers showing particular or improved properties. They are generally employed in weak proportions and it is hoped that they lead to homogeneous cross-linked polymers. They must therefore possess adequate properties of solubility, of reactivity, of compatibility towards the monomers or polymers with which one wishes to react them.

2. The Prior Art

It is known that cross-linked polymers are easily obtained by radical-like polymerization, notably in solution or in suspension, of one or more ethylene monomers in the presence of an appropriate cross-linking agent, containing at least two polymerizable ethylene functions such as the di- or polyvinyls compounds, di- or polyesters of, mono- or polycarboxylic ethylene acids with polyols, bisacrylamides such as N,N-methylene bisacrylamide or bisacrylamidoacetic acid. Among all these known polyethylene cross-linking agents, salified bisacrylamidoacetic acid is, to the knowledge of the Applicant, the only one which is very soluble in water but it is a derivative of acrytamide which due to its toxicity one would prefer to be absent in certain particular uses.

Therefore a hydrosoluble diethylene cross-linking agent is sought which is compatible notably with acrylic acid or its ammonium salts or alkali metals, which does not have an acrylamide fragment in its structure, for the manufacture of cross-linked polymers, insoluble in water but capable of being water-swellable such as thickening or super absorbent polymers notably intended for cosmetic and/or hygienic uses, such as the manufacture of babies diapers.

Sodium diallyloxyacetate has already been prepared by L. Holmquist, Acta Chem. Scand., 1969, 23, 1045–52, by condensation of dichloroacetic acid with excess sodium 2-propene-1-olate, in order to test its possible inhibiting activity on the neuraminidase of vibrio cholerae. Moreover allyl diallyloxyacetate is described in the American U.S. Pat. No. 4,454,065 and in the European Patent Application No. 0,094,815. In these documents, it is noted as having a boiling point of 55°–60° C. under 16 mm/Hg which is very different to that found by the Applicant.

SUMMARY OF THE INVENTION

The Applicant has found with astonishment new hydrosoluble ethylene cross-linking agents corresponding to the needs of users and which do not present the inconveniences of those of the prior art.

The hydrosoluble ethylene cross-linking agents, according to the present invention are products of general formula (I)

$$CH_2=CH-CH_2-O \diagdown CH-COOM \diagup CH_2=CH-CH_2-O \quad (I)$$

in which M represents a hydrogen, potassium or lithium atom or an ammonium group.

This is why a subject of the present invention is diallyloxyacetic acid and its salts with inorganic bases with the exception of the sodium salt.

Among these products, the following can be more particularly mentioned:
diallyloxyacetic acid;
potassium diallyloxyacetate;
ammonium diallyloxyacetate.
Also lithium diallyloxyacetate can be mentioned.

According to the invention, the products of general formula (I) above can be prepared by a process characterised in that an alkaline hydrolysis of allyl diallyloxyacetate is effected so as to obtain the corresponding basic salt which is either isolated, or if desired is acidified to diallyloxyacetic acid which is isolated or if desired, salified to an ammonium salt.

DETAILED DESCRIPTION OF THE INVENTION

In the preferred conditions of employment, the above process is characterised in that glyoxylic acid is reacted with allyl alcohol so as to obtain allyl diallyloxyacetate.

The glyoxylic acid is preferably reacted with an excess of allyl alcohol in the presence of an acid catalyst and, optionally, of a solvent that is non-miscible in water giving an azeotrope with water, so as to obtain allyl diallyloxyacetate.

The hydrolysis is achieved by reacting allyl diallyloxyacetate with the corresponding alkali metal hydroxide. If desired the basic salts are acidified to diallyloxyacetic acid, preferably using an organic acid, the corresponding salt of which is only slightly soluble in water.

In the preferred operating conditions of the invention, the above-described process is achieved in the following way:

1. The reaction of the allyl alcohol with glyoxylic acid is achieved:
    with an excess of 5 to 12 moles, advantageously with 10 moles of alcohol per mole of glyoxylic acid,
    in the presence of a solvent chosen from toluene, cyclohexane and 1,1,1-trichloroethane,
    in the presence of an acid catalyst chosen from para-toluenesulphonic acid, sulphuric acid and sulphonic ion-exchange resins, in acid form,
    with concomitant azeotropic distillation of the water present and formed in the reaction medium.

2. The hydrolysis of allyl diallyloxyacetate isolated in the first stage of the process by known means is realized:
    at ambient temperature with a slight deficiency of sodium hydroxide, potassium hydroxide or lithium hydroxide,
    with the elimination of released allyl alcohol by azeotropic distillation with water.

3. The acidification of sodium, potassium or lithium diallyloxyacetate into diallyloxyacetic acid is achieved:

at ambient temperature, in bi-phase medium of water and organic solvent, non-miscible with water, with a slight deficiency of oxalic acid.

4. Ammonium diallyloxyacetate is obtained salification of the diallyloxyacetic acid with ammonia either in liquid form at about −30° C., or in solution in an organic solvent, or in water, then by evaporation under vacuum of the reaction medium obtained.

Also a subject of the present invention is the use of products of general formula (I) as cross-linking agents. In effect these products can be easily copolymerised, even in very weak proportions, with various ethylene monomers to produce cross-linked copolymers with particular or improved properties. They can be used as co-monomers equally as in polymerisation processes in solution, in suspension or in water-in-oil emulsion or oil-in-water emulsion, with monomers such as acrylic acid, sodium acrylate, potassium acrylate, ammonium acrylate, free, salified or quaternarized dimethylaminoethyl acrylate, acrylamide and similar derivatives corresponding to methacrylic acid, sodium vinylsulphonate, diallyldimethyl-ammonium chloride, 2-(meth)acrylamido-2-methyl-1-propanesulphonic acid, 2-hydroxy-(meth)acryloyl-3-oxy-1-propanesulphonic acid, itaconic acid, citraconic acid, maleic acid. Among all the above ethylene monomers, the preferred monomers are acrylic acid, alkali metal acrylates and ammonium acrylate.

The products of general formula (I) are particularly useful for obtaining hydrophilic polymers insoluble in water but water swellable such as thickening polymers, superabsorbent polymers, based on free acrylic acid, partially or totally salified. In effect, with these monomers, the products of general formula (I) copolymerise with each other easily and in a homogeneous fashion, even in proportions which can be 0.001% by molar proportions, to produce cross-linked polymers that are virtually insoluble in water, that is to say showing a percentage of extractibles of less than 10% by weight relative to the dry weight of the polymer, and showing moreover excellent absorption properties.

The following examples illustrate the invention without however limiting it. In these examples, the tests used are carried out in the following manner:

the water absorption capacity of the polymer is determined at 20° C., by agitating for 30 minutes, 0.4 g of polymer in 500 g of water, then weighing the drained polymer gel obtained. The found weight is expressed for 1 g of polymer;

the absorption capacity for a saline aqueous solution is determined at 20° C., by agitating for 30 minutes, 2 g of polymer in 500 g of an aqueous solution containing 9 g/l of sodium chloride, then by weighing the drained polymer gel obtained. The found weight is expressed as previously for 1 g of polymer.

The percentage of extractibles is determined according to the following method:

1 g of polymer to be tested is placed in 200 g of an aqueous solution containing 9 g/l of sodium chloride, this suspension is agitated for 16 hours at 20° C.;

the polymer gel obtained is drained and the filtrate collected, 100 cm$^3$ of filtrate is analysed for the carboxylic and carboxylate functions present;

the result of this analysis is expressed by gram of dissolved polymer per 100 g of dry polymer.

EXAMPLE 1

A mixture of:

92.6 g of glyoxylic acid at 80% by weight in water, i.e. 1 mole, 581 g (10 moles) of allyl alcohol, 110 g of 1,1,1-trichloroethane, 2.5 g of 98% concentrated sulphuric acid, is heated under reflux with azeotropic distillation of the water and recycling of the entrainment solvent.

After 330 minutes of heating, the theoretical quantity of water is collected, the reaction medium is then cooled down then it is neutralised with sodium hydrogencarbonate and the mineral salts obtained are then filtered. The filtrate is then concentrated under vacuum to eliminate the excess ally alcohol and the solvent, then the residual oil is distilled. In this way 50.7 g (0.29 mole) of allyl 2-allyloxy glycolate, distilling over at 50° C. under 5 mbar then 148.6 g (0.7 mole) of allyl diallyloxyacetate at 108° C. under 5 mbar are collected.

Allyl 2-allyloxy glycolate is mentioned in European Patent No. 0,109,044 without physical constants.

EXAMPLE 2

Preparation of sodium diallyloxyacetate 21.2 g (0.1 mole) of allyl diallyloxyacetate is dissolved in 42 g of toluene then 3.92 g (98 mmoles) of sodium hydroxide dissolved in 50 g of water is introduced into this solution. This bipbase reaction medium is agitated vigorously for 30 minutes at 30° C., then decanted and the aqueous phase is collected and subjected to a vacuum distillation to eliminate the freed allyl alcohol by azeotropic distillation. The aqueous phase is then poured into acetone to precipitate the expected sodium diallyloxyacetate.

After filtering, the precipitate obtained is then dried under vacuum at 60° C. up to constant weight. In this way 19 g (98 mmoles) of pure crystallised sodium diallyloxyacetate is obtained having a melting point of 179°–181° C. (cited literature 179°–181° C.)

This product is very soluble in water.

EXAMPLE 3

Preparation of diallyloxyacetic acid 100 g of diethyl oxide then a solution of 17.6 g (0.14 mole) of oxalic acid crystallised with two molecules of water in 62 g of water are introduced at ambient temperature and under agitation into an aqueous solution containing 29.1 g (0.15hole) of sodium diallyloxyacetate in 71 g of water. The biphasic medium obtained is agitated vigorously for 10 minutes then it is decanted. The ethereal phase is then dried over anhydrous sodium sulphate, filtered and finally concentrated to dryness under vacuum. In this way 24 g (0.14 mole) of pure diallyloxyacetic acid is obtained. This acid is in the form of an oil, it has a pka of 2.9 and it is soluble in water and in standard organic solvents such as diethyl oxide, dichloromethane; however, in aqueous solution, it hydrolyses.

| | Microanalysis | |
| --- | --- | --- |
| | C % | H % |
| $C_8H_{12}O_4$ Calculated | 55.80 | 7.03 |
| Found | 55.8 | 7.0 |

Physical analysis NMR $^{13}C$ (CDCl$_3$) at 50.4 MHz
COOH: 170.8 ppm =CH—: 133.25 ppm CH$_2$=116.3 ppm

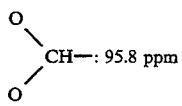

CH$_2$—O: 67.8 ppm

EXAMPLE 4

230 g (3.2 moles) of acrylic acid is dissolved at ambient temperature in 150 g of water containing 129 g (2.3 moles) of potassium hydroxide, then the following is introduced into this solution:
- 10 g of an aqueous solution of diethylenetriaminopentaacetic acid at 9.6 g/l,
- 467 mg of sodium persulphate dissolved in 5 g of water,
- 115 mg (0.59 mmole) of sodium diallyloxyacetate dissolved in 5 g of water,
- 104.4 g of water.

In this way 634 g of an aqueous solution designated A is obtained.

The following are heated in a polymerization reactor, under reflux, with agitation, for 30 minutes in an inert atmosphere:
- 634 g of cyclohexane,
- 3.5 g of ethylcellulose containing from 48 to 49.5% of ethoxylated groups and showing a viscosity of 200 mPa.s at 25° C., Then solution A is introduced over 90 minutes, under agitation and in an inert atmosphere. After the introduction is finished, the mixture continues under reflux for 1 hour, then 240 g of water is eliminated by azeotropic distillation and finally the suspension obtained is cooled down to ambient temperature. The desired polymer is filtered out then dried at constant weight at 80° C. In this way 332 g of cross-linked sodium acrylate-acrylic acid polymer is obtained, showing the following characteristics:
- water absorption capacity: 213 g/g,
- absorption capacity for an aqueous saline solution at 9 g/l: 40.5 g/g,
- percentage of extractibles: 2.6%

EXAMPLE 5

An aqueous solution is prepared containing:
- 366 g of de-ionised water,
- 52 g (0.93 mole) of potassium hydroxide,
- 0.8 g (4.1 mmoles) of sodium diallyloxyacetate,
- 80 g (1.11 mole) of acrylic acid,
- 57 mg (0.11 mmole) of sodium diethylenetriaminopentaacetate;

In this carefully de-oxygenated solution the following is introduced under agitation at 40° C.:
- 160 mg (6.7 mmoles) of sodium persulphate dissolved in 2 g of water,
- 120 mg (6.3 mmoles) of sodium metabisulphite dissolved in 2 g of water.

After a short wait, the polymerization starts and the reaction medium turns into a gel with significant heating. When the temperature of the reaction medium has returned to ambient temperature, the polymer gel obtained is dried for 16 hours at 40° C., then for 10 hours at 100° C. In this way, after crushing, a white powder constituted by a cross-linked potassium acrylate-acrylic acid copolymer is obtained presenting the following characteristics:
- dry extract: 93.8%,
- water absorption capacity: 113 g/g,
- absorption capacity for an aqueous solution of sodium chloride at 9 g/l: 28.8 g.

We claim:

1. A method of producing a cross-linked polymer comprising cross-linking an ethylene monomer with a compound of the formula:

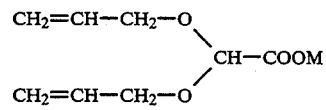

wherein M is selected from hydrogen, potassium, lithium or ammonium,
wherein the cross-linking compound is present in an amount of from 0.001% to 0.4%,
wherein the ethylene monomer is selected from the group consisting of acrylic acid, sodium acrylate, potassium acrylate, ammonium acrylate, free, salified or quaternarized dimethylaminoethyl acrylate, acrylamide and similar derivatives corresponding to methacrylic acid, sodium vinylsulphonate, diallydimethyl-ammonium chloride, 2-(meth)acrylamido-2-methyl-1-propanesulphonic acid, 2-hydroxy(meth)acryloyl-3-oxy-1-propanesulphonic acid, itaconic acid, citraconic acid, and maleic acid.

2. A method in accordance with claim 1, wherein potassium, lithium or ammonium diallyloxyacetate is the cross-linking agent.

3. The method of claim 1 wherein said ethylene monomer is acrylic acid, an alkali metal acrylate, or ammonium acrylate.

4. In a method of preparing a hydrophillic polymer which is insoluble in water but capable of becoming swollen in water, comprising reacting an acrylic monomer with a cross-linking co-monomer, the improvement wherein
said cross-linking co-monomer is present in an amount of at least 0.001% by molar proportions and consists essentially of a compound of the formula:

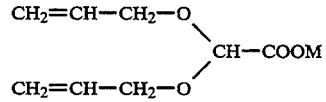

wherein M is selected from hydrogen, potassium, sodium, lithium or ammonium, and the resultant cross-linked hydrophillic polymer has less than 10% by weight of extractables based on the dry weight of the polymer.

5. A method according to claim 4 wherein said acrylic monomer is a partially salified acrylic acid.

6. A method according to claim 4 wherein said monomer is a substantially totally salified acrylic acid.

* * * * *